United States Patent
Buono et al.

(10) Patent No.: US 6,232,427 B1
(45) Date of Patent: May 15, 2001

(54) ESTERIFICATION METHOD

(75) Inventors: John A. Buono, Riverside; Maryellen Cobb, Warwick, both of RI (US); Tao T. Tao, North Attleboro, MA (US)

(73) Assignee: Teknor Apex Company, Pawtucket, RI (US)

( * ) Notice: Subject to any disclaimer, the term of this patent is extended or adjusted under 35 U.S.C. 154(b) by 0 days.

(21) Appl. No.: 09/470,613

(22) Filed: Dec. 22, 1999

Related U.S. Application Data

(63) Continuation-in-part of application No. 09/199,691, filed on Nov. 25, 1998, now abandoned.
(60) Provisional application No. 60/067,970, filed on Dec. 8, 1997.

(51) Int. Cl.[7] .................................................. C08G 14/02
(52) U.S. Cl. ............................................................ 528/147
(58) Field of Search ............................................. 524/147

(56) References Cited

U.S. PATENT DOCUMENTS

| | | | |
|---|---|---|---|
| 4,997,953 | 3/1991 | McKenna | 548/461 |
| 5,021,295 | 6/1991 | Nakane et al. | 428/379 |
| 5,076,970 | 12/1991 | Roos et al. | 252/609 |
| 5,137,948 | 8/1992 | Bonnet et al. | 524/90 |
| 5,290,945 | 3/1994 | Roy et al. | 548/462 |
| 5,317,048 | 5/1994 | Tarbit et al. | 524/94 |
| 5,728,323 | 3/1998 | Day et al. | 252/601 |

OTHER PUBLICATIONS

Database CAPLUS on STN, 1998:243537, Wang et al., "Process for Preparation of Tetrabromophthalates" Abstract of CN 1124729 A, Jun. 6, 1996.

*Primary Examiner*—Terressa M. Boykin
(74) *Attorney, Agent, or Firm*—Fish & Richardson P.C.

(57) ABSTRACT

Methods of making halogenated aromatic esters are described. Polymer compositions including halogenated aromatic esters are also described. In one embodiment, the method includes contacting a tetrabromophthalate, an alcohol and barium acetate.

39 Claims, No Drawings

ESTERIFICATION METHOD

CROSS REFERENCE TO RELATED APPLICATIONS

This application is a continuation-in-part of application U.S. Ser. No. 09/199,691, filed Nov. 25, 1998, now abandoned, which claims priority, under 35 U.S.C. 119(e)(1), from provisional application No. 60/067,970, filed Dec. 8, 1997, hereby incorporated by reference in its entirety.

BACKGROUND OF THE INVENTION

The invention relates to methods of making esters and the use of these esters in polymer compositions.

Tetrabromophthalic anhydride can be reacted with an alcohol to form tetrabromophthalate. At reaction temperatures, tetrabromophthalic anhydride can undergo decarboxylation. Sulfuric acid, which is often used during synthesis of the tetrabromophthalic anhydride, can also be used to reduce decarboxylation of the anhydride. However, the sulfuric acid can degrade the alcohol used during esterification, potentially resulting in reduced yield of tetrabromophthalate and decreased yield of recycled alcohol. Therefore, the alcohol and tetrabromophthalic anhydride are usually reacted in the presence of a neutralizing agent. Such neutralizing agents include, for example, sodium acetate and potassium acetate.

SUMMARY OF THE INVENTION

The invention relates to methods of esterifying carboxylated, halogenated aromatic compounds to form halogenated aromatic esters. These methods can result in good purity of the final product and high yields of the desired halogenated aromatic esters. In addition, the methods can reduce costs by using the reactants, such as alcohols, in a more efficient manner.

The invention also relates to the use of the halogenated aromatic esters in polymer compositions. These polymer compositions can offer benefits including flame resistance and smoke suppression.

In one aspect, the invention features a method of esterifying a carboxylated, halogenated aromatic compound, such as a tetrabromophthalate. The method includes contacting the carboxylated, halogenated aromatic compound with an alcohol and a sulfuric acid deactivating compound capable of forming a water insoluble sulfate compound.

As used herein, "halogenated aromatic compound" refers to an aromatic compound that has at least one halogen atom directly bonded to an aromatic carbon atom.

As used herein, "carboxylated, halogenated aromatic compound" denotes a halogenated aromatic compound that has at least one carboxyl carbon atom directly bonded to an aromatic carbon atom. Typically, carboxylated, halogenated aromatic compounds are halogenated aromatic carboxylic acids or halogenated aromatic carboxylic anhydrides.

As used herein, "sulfuric acid deactivating compound capable of forming a water insoluble sulfate compound" refers to a compound that can react with sulfuric acid to reduce the concentration of sulfuric acid and form a sulfate-containing compound that has a solubility product in water of less than about $1 \times 10^{-4}$ when measured at a temperature of about 25° C.

In another aspect, the invention features a method of esterifying tetrabromophthalic anhydride. The method includes contacting tetrabromophthalic anhydride with an alcohol in the presence of barium acetate.

In some embodiments, the method can also include contacting an esterification catalyst with the reactants to increase the rate of esterification. In these embodiments, an esterification catalyst deactivating compound can be added after formation of the halogenated aromatic ester to prevent the esterification catalyst from catalyzing hydrolysis of the halogenated aromatic ester.

In certain embodiments, the method can also include contacting an anti-oxidant to reduce color formation of the halogenated aromatic ester.

In yet another aspect, the invention features a polymer composition that includes a halogenated aromatic ester made according to one of the above-noted methods.

In yet a further aspect, the invention features a polymer composition that includes a polyvinyl chloride, a pentaerythritol ester, aluminum trihydrate, an antimony trioxide flame retardant, an isodecyl diphenyl phosphate plasticizer, a zinc borate flame retardant and a halogenated aromatic ester including at most about 0.1 weight percent of ether compounds. The halogenated aromatic ester can be derived from a linear alcohol.

As used herein, the term "linear alcohol" refers to alcohols with hydrocarbon chains that are noncyclic and non-branched.

In other aspects, the invention features a polymer composition that includes an aromatic ester derived from a non-linear alcohol or a mixture of aromatic esters that are derived from both linear alcohols and non-linear alcohols.

As used herein, the term "non-linear alcohol" refers to alcohols that are not linear alcohols.

The halogenated aromatic ester(s) included in the polymer compositions of the invention can include less than about 0.1 weight percent (e.g., less than about 0.05 weight percent) of ether compounds.

The halogenated aromatic ester(s) included in the polymer compositions of the invention can include less than about 10 weight percent (e.g., less than about five weight percent or less than about two weight percent) of undesired halogenated aromatic esters.

In yet another aspect, the invention features a plasticizer, which when used, e.g., in PVC compositions, can provide the composition with good performance at low temperature. The plasticizer includes a brominated aromatic ester and a chlorinated aromatic ester, typically with the latter in sufficient amounts to make the plasticizer a liquid at room temperature. Therefore, the plasticizer can be handled easily during production and well blended with the composition. The preferred brominated aromatic ester is a tetrabromophthalate, and the preferred chlorinated aromatic ester is a tetrachlorophthalate. Such compositions are useful as flame retardants and are good for cable jacketing and wire insulation.

Other features and advantages of the invention will be apparent from the description of the preferred embodiments.

DESCRIPTION OF THE PREFERRED EMBODIMENTS

The halogenated aromatic esters are made by reacting a carboxylated, halogenated aromatic compound with an alcohol in the presence of a sulfuric acid deactivating compound capable of forming a water insoluble sulfate compound.

Examples of carboxylated, halogenated aromatic compounds include monobromophthalic acid, dibromophthalic acid, tribromophthalic acid, tetrabromophthalic acid, pentabromobenzoic acid, monochlorophthalic acid, dichlorophthalic acid, trichlorophthalic acid, tetrachlorophthalic acid, pentachlorobenzoic acid, monobromophthalic anhydride, dibromophthalic anhydride, tribromophthalic anhydride, tetrabromophthalic anhydride, monochlorophthalic anhydride, dichlorophthalic anhydride, trichlorophthalic anhydride and tetrachlorophthalic anhydride.

Examples of sulfuric acid deactivating compounds include barium acetate, barium bromide, barium propionate, barium butyrate, barium chlorate, barium chloride, barium dithionate, barium formate, barium hydroxide, barium iodide, barium nitrate, barium nitrite, barium oxide, barium hypophosphite, barium salicylate, barium peroxydisulfate, barium monosulfide, barium disulfide, barium trisulfide, lead acetate, lead chlorate, lead perchlorate, lead citrate, lead ethylsulfate, lead formate, lead butyrate, lead lactate, lead nitrite, lead nitrate, lead peroxyl disulfate, lead dithionate, mercury chlorate, strontium acetate, strontium bromate, strontium bromite, strontium chlorate, strontium perchlorate, strontium chloride, strontium formate, strontium hydroxide, strontium iodide, strontium lactate, strontium nitrate, strontium nitrate, strontium oxide, strontium salicylate, strontium monosulfite, strontium trisulfite, strontium tetrasulfite, strontium dithionate, calcium acetate, calcium benzoate, calcium bromide, calcium bromate, calcium butyrate, calcium chlorate, calcium perchlorate, calcium chloride, calcium formate, calcium fumarate, calcium gluconate, calcium iodide, calcium butyrate, calcium lactate, calcium valerate, calcium nitrate, calcium nitrite, calcium hypophosphite, calcium propionate, calcium salicylate and calcium dithionate.

The alcohol can be a straight-chained alcohol, a branched alcohol, a cyclic alcohol, a saturated alcohol, an unsaturated alcohol, a substituted alcohol and/or an unsubstituted alcohol. In addition, the alcohol can include more than one alcoholic hydroxyl group, such as polyols and glycols. Furthermore, a combination of two or more alcohols can be used.

In certain embodiments, at least one linear alcohol is used. Examples of linear alcohols include methyl alcohol, ethyl alcohol, n-butyl alcohol, n-propyl alcohol, n-pentyl alcohol, n-hexyl alcohol, n-heptyl alcohol, n-octyl alcohol, n-nonyl alcohol, n-decyl alcohol, n-undecyl alcohol, n-dodecyl alcohol, n-tridecyl alcohol and n-tetradecyl alcohol.

Examples of non-linear alcohols include iso-propyl alcohol, iso-butyl alcohol, iso-pentyl alcohol, iso-hexyl alcohol, iso-heptyl alcohol, 2-ethylhexyl alcohol, iso-octyl alcohol, iso-nonyl alcohol, iso-decyl alcohol, iso-undecyl alcohol, iso-dodecyl alcohol, iso-tridecyl alcohol and iso-tetradecyl alcohol.

Examples of glycols include ethylene glycol, di ethylene glycol, triethylene glycol, polyethylene glycol, propylene glycol, butylene glycol, hexene glycol, heptene glycol, octene glycol, nonene glycol, decene glycol, mono-pentaerythritol, di-pentaerythritol, tri-pentaerythritol, glycerine, sorbitol, ethylene oxide adducts and propylene oxide adducts.

Esterification catalysts can be titanium compounds, tin compounds, hafnium and zirconium compounds. In some embodiments, a combination of two or more esterification catalysts can be used. Examples of esterification catalysts are alkyl titanates, tetra-isopropyl titanate, tetrapropyl titanate, tetra-n-butyl titanate, tetramethyl titanate, tetra-2-ethylhexyl titanate, mono-n-butyl tin oxide, di-n-butyl tin oxide, di-n-butyl dichloride tin, mono-n-octyl tin oxide, di-n-octyl tin oxide, tin oxalate, tin oleate, tin oxide, dibutyl tin diacetate, n-propyl zirconate, zirconium acetylacetaonate, hafnium tetrabutoxide, and titanate chelates of acetyl acetonate, ethyl acetoacetate, triethanolamine, lactic acid, oxalic acid and citric acid.

Examples of esterification catalyst deactivating compounds include alkali and alkaline earth hydroxides and carbonates, such as potassium carbonate, lithium carbonate, sodium carbonate, potassium hydroxide, lithium hydroxide, potassium hydroxide, magnesium carbonate, calcium carbonate, beryllium carbonate, magnesium hydroxide, calcium hydroxide and beryllium hydroxide. In some embodiments, a combination of two or more esterification catalyst deactivating compounds can be used.

Optionally, an anti-oxidant can be added to the mixture to reduce coloration of the halogenated aromatic ester. Anti-oxidants include hypophosphorous acid, hindered phenols, butylhydroxytoluene, bisphenol A, and organic phosphites.

The method can be carried out under any of the standard conditions used for esterification reactions. The reaction apparatus should be capable of agitating and heating the reactants and condensing the distillate. In addition, the reaction apparatus should be capable of removing excess alcohol and reaction products, such as water.

The carboxylated, halogenated aromatic compound is contacted with an alcohol in the presence of a sulfuric acid deactivating compound capable of forming a water insoluble sulfate compound. For example, tetrabromophthalic acid anhydride is contacted with 2-ethylhexyl alcohol in the presence of barium acetate. An esterification catalyst (tetrabutyl titanate) and anti-oxidant (hypophosphorous acid) are also included in the mixture. The mixture is agitated in an inert atmosphere, such as a nitrogen atmosphere, to minimize undesired side reactions.

In some embodiments, the esterification catalyst (tetrabutyl titanate) can be added in the presence of water and optionally the sulfuric acid deactivating compound (barium acetate) without deactivating the tetrabutyl titanate. In these embodiments, the method offers the advantage of not requiring that water be removed from the mixture prior to the addition of tetrabutyl titanate, reducing the cost and complexity of the method.

The reaction can be conducted in an excess of alcohol. Thus, prior to reaction, so the initial molar ratio of alcohol to carboxylated, halogenated aromatic compound is preferably at least about 1, more preferably from about 1 to about 200, and most preferably from about 3 to about 1.

Prior to reaction, the mixture preferably includes from about $1.4 \times 10^{-3}$ weight percent to about 3.0 weight percent esterification catalyst relative to the initial amount of carboxylated, halogenated aromatic compound.

Prior to reaction, the mixture preferably includes from about $1.4 \times 10^{-3}$ weight percent to about 0.14 weight percent anti-oxidant relative to the initial amount of carboxylated, halogenated aromatic compound.

Prior to reaction, the mixture preferably includes from about $1.4 \times 10^{-3}$ weight percent to about 1.4 weight percent of the sulfuric acid deactivating compound relative to the initial amount of carboxylated, halogenated aromatic compound.

During agitation, the mixture is heated. If the temperature of the mixture is too high the carboxylated, halogenated aromatic compound may decompose. However, if the temperature is too low, the reaction may not proceed at an acceptable rate. Therefore, the mixture is preferably heated to a temperature of from about 160° C. to about 250° C., more preferably from about 180° C. to about 240° C., and most preferably from about 200° C. to about 220° C.

The mixture is held at this temperature, and aliquots of the mixture are taken periodically. When at least about 99% of the carboxylated, halogenated aromatic compound has been converted to the halogenated aromatic ester, the temperature is reduced, an esterification catalyst deactivation compound is added to the mixture to prevent the esterification catalyst from catalyzing hydrolysis of the halogenated aromatic ester, and the mixture is agitated. Upon addition of the esterification catalyst deactivation compound, the mixture preferably includes from about $1.4 \times 10^{-3}$ weight percent to about 1.4 weight percent of the esterification catalyst deactivation catalyst relative to the initial amount of carboxylated, halogenated aromatic compound. In some embodiments, the esterification catalyst deactivation compound is an aqueous slurry of magnesium carbonate and magnesium hydroxide.

During addition of the esterification catalyst deactivation compound, the temperature should be low enough to minimize hydrolysis of the halogenated aromatic ester but high enough to deactivate the esterification catalyst and give good phase separation of the mixture. Preferably, the temperature of the reaction mixture is from about room temperature to about 200° C., more preferably from about 60° C. to about 70° C., and most preferably about 65° C.

The mixture is held at this temperature, and aliquots of the mixture are taken periodically. When the pH of the mixture reaches a value greater than about 7, alcohol remaining in the mixture is removed from the mixture. In some embodiments, this involves heating the mixture under a vacuum. In these embodiments, the combination of temperature and pressure should be sufficient to remove the majority of the alcohol from the mixture without decomposing the halogenated aromatic ester or causing the ester to undergo undesirable reactions. Therefore, the temperature of the mixture is preferably from about 170° C. to about 210° C., more preferably from about 180° C. to about 200° C. The pressure of the reactor is preferably at most about 100 torr, more preferably below about 40 torr, and most preferably below about 30 torr.

When less than about 5 weight percent of the mixture is alcohol, steam is introduced into the mixture to assist in removing at least some of the remaining alcohol and volatiles. Preferably, the steam is introduced such that the mixture is at a temperature of from about 130° C. to about 210° C., more preferably from about 160° C. to about 180° C. The pressure of the reactor during the steam introduction is preferably less than about 50 torr.

When the mixture includes less than about one weight percent alcohol, more preferably less than about one tenth weight percent alcohol, the mixture is cooled to about room temperature, and the vacuum is broken. To improve filtration of the ester and purity of the final product, the mixture is then heated and exposed to a caustic solution. Examples of such caustic solutions are aqueous sodium hydroxide and aqueous potassium hydroxide. In one embodiment, the caustic solution is an aqueous sodium hydroxide solution with 5 weight percent sodium hydroxide.

During the caustic wash, the temperature should be high enough to allow the caustic solution to dissolve remaining catalysts and water soluble salts without decomposing the halogenated aromatic ester or causing the ester to undergo undesirable reactions. Preferably, the temperature is from about 60° C. to about 90° C., more preferably from about 70° C. to about 80° C., and most preferably about 75° C.

The resulting solution is allowed to settle so that separation occurs between the organic phase and the aqueous phase. The organic phase, which contains the halogenated aromatic ester, is isolated and a de-colorizing carbon is added to the organic phase to remove colored bodies from the organic phase. Upon addition of the de-colorizing carbon, the mixture preferably includes from about $1.4 \times 10^{-3}$ to about 3 weight percent of the de-colorizing carbon relative to the initial amount of carboxylated, halogenated aromatic compound.

Water remaining in the organic phase is removed by vacuum or the introduction of a dry gas, such as nitrogen or an inert gas, into the mixture. In dry gas processes, the organic phase is typically at a temperature of from about room temperature to about 150° C. In vacuum process, the pressure is reduced to below about 100 torr, and the organic phase is held at a temperature of from about room temperature to about 150° C.

The product is allowed to settle and is subsequently filtered off. The product includes the desired halogenated aromatic ester and can include certain other compounds as well. The method can result in a product that has a relatively large amount of the desired halogenated aromatic ester with relatively small amounts of other compounds.

Preferably, the product includes at least about 95 weight percent of the desired halogenated aromatic ester, more preferably at least about 98 weight percent of the desired halogenated aromatic ester, and most preferably at least about 99 weight percent of the desired halogenated aromatic ester.

Preferably, the product includes less than about 0.1 weight percent of ether compounds, more preferably less than about 0.05 weight percent of ether compounds.

Preferably, the product includes less than about 10 weight percent of undesired halogenated aromatic esters, more preferably less than about five weight percent of undesired halogenated aromatic esters, and most preferably less than about two weight percent of undesired halogenated aromatic esters.

In embodiments in which tetrabromophthalic anhydride is used as a reactant, the desired halogenated aromatic ester is tetrabromophthalate, and the undesired halogenated aromatic ester can be tribromophthalate and/or tetrabromobenzoate.

As noted above, the method includes removing at least some of the alcohol from the reaction mixture. This alcohol can be condensed and re-used in subsequent esterification reactions. The method can result in a relatively high purity and yield of the alcohol. Preferably, the condensed product is at least about 90 weight percent of the alcohol, more preferably at least about 95 weight percent of the alcohol, and most preferably at least about 99 weight percent of the alcohol.

In some embodiments, the invention relates to polymer compositions that include one or more halogenated aromatic esters, such as, for example, di-2-ethylhexyl tetrabromophthalate, di-n-decyl tetrabromophthalate, di-n-octyl tetrabromophthalate, di-n-nonyl tetrabromophthalate, di-n-undecyl tetrabromophthalate, di-n-dodecyl tetrabromophthalate, n-octyl n-decyl tetrabromophthalate, n-decyl n-dodecyl tetrabromophthalate, n-octyl n-dodecyl tetrabromophthalate, di-2-ethylhexyl tetrachlorophthalate, di-n-decyl tetrachlorophthalate, di-n-octyl tetrachlorophthalate, di-n-nonyl tetrachlorophthalate, di-n-undecyl tetrachlorophthalate, di-n-dodecyl tetrachlorophthalate, n-octyl n-decyl tetrachlorophthalate, n-decyl n-dodecyl tetrachlorophthalate and n-octyl n-dodecyl tetrachlorophthalate. Preferably, the halogenated aromatic compounds contained in these compositions include at most about 0.1 weight percent of ether compounds, more preferably at most about 0.05 weight percent of ether compounds. These polymer compositions can provide flame retardance and/or smoke suppression.

Examples of polymer compositions in which halogenated aromatic compounds can be included are disclosed in the following references. U.S. Pat. No. 4,098,704, which is hereby incorporated by reference, discloses the use of polyoxyalkylene tetrahalophthalates in polyester fabrics. U.S. Pat. No. 4,762,862, which is hereby incorporated by reference, discloses the use of tetrabromophthalates in polystyrene resins. U.S. Pat. No. 4,764,550, which is hereby incorporated by reference, discloses the use of tetrabromophthalates in polyphenylene resins. U.S. Pat. No. 4,912,158, which is hereby incorporated by reference, discloses the use of tetrabromophthalates in polycarbonate resins. U.S. Pat. No. 4,923,917, which is hereby incorporated by reference, discloses the use of tetrabromophthalates styrene-maleic anhydride copolymer resins. U.S. Pat. No. 4,938,894, which is hereby incorporated by reference, discloses the use of tetrabromophthalates for use in acrylonitrile-butadiene styrene terpolymer resins. U.S. Pat. No. 3,775,165, which is hereby incorporated by reference, discloses the use of tetrabromophthalates for use in polypropylene. U.S. Pat. No. 3,989,653, which is hereby incorporated by reference, discloses the use of tetrabromophthalates in polyurethane. U.S. Pat. No. 2,062,403 discloses the use of tetrabromophthalates in cellulose acetate. Commonly assigned U.S. patent application Ser. No. 08/511,967, which is hereby incorporated by reference, discloses the use of tetrabromophthalates in a polymer composition that includes a polyvinyl chloride resin, a pentaerythritol ester plasticizer, aluminum trihydrate, an antimony trioxide flame retardant, an isodecyl diphenyl phosphate plasticizer, an ammonium octamolybdate flame retardant and a zinc borate flame retardant.

In certain embodiments, the invention relates to a polymer composition that includes 100 parts polyvinylchloride resin, about 10–50 parts of a pentaerythritol ester plasticizer, about 25–80 parts of aluminum trihydrate, about 1–10 parts of an antimony trioxide flame retardant, about 2–20 parts of an isodecyl diphenyl phosphate plasticizer, about 4–15 parts of an ammonium octamolybdate flame retardant, about 1–5 parts of a zinc borate flame retardant, and about 2–15 parts of a halogenated aromatic ester, such as a tetrabromophthalate.

EXAMPLE I

Di-2-ethylhexyl tetrabromophthalate was prepared as follows. About 1.54 grams of barium acetate was dissolved in about 25 grams of water. About 585 grams of di-2-ethylhexyl alcohol, about 696 grams of tetrabromophthalic anhydride, about 4.67 grams of tetrabutyl titanate and about 0.07 grams of an about 50 weight percent aqueous solution of hypophosphorous acid were added to the barium acetate solution.

This mixture was heated to about 210° C. and agitated until about 99 percent of the tetrabromophthalic anhydride was converted to tetrabromophthalate. The reaction water was collected during the reaction.

The mixture was cooled to about 65° C., and about one gram of an aqueous mixture of magnesium carbonate and magnesium hydroxide in about 20 grams of water were added to the mixture, and the mixture was agitated for about one hour.

The mixture was heated to from about 180° C. to about 200° C. under a vacuum of about 25 torr until there was less than about one weight percent alcohol remaining in the mixture.

Steam was introduced into the mixture such that the temperature of the mixture was about 170° C. The steam was introduced until the mixture included less than about one weight percent alcohol.

The vacuum was broken, and the mixture was cooled to about 75° C. The mixture was washed with an aqueous solution of sodium hydroxide (about 5 weight percent). Phase separation was then allowed to occur, and the organic phase was collected.

About 5 grams of de-colorizing carbon was added to the organic phase. The organic phase was then agitated and heated to about 115° C. under a vacuum of about 25 torr to dry the product. The product was then filtered. The filtered product included about 96.5 weight percent di-2-ethylhexyl tetrabromophthalate.

A preferred polymer composition for use as a fire retardant, e.g., for wire and cable compounds, includes a polymer, a plasticizer, a clay filler, hydrated alumina and/or magnesium hydroxide, and one or more stabilizers or other additives such as lubricants and smoke suppressants.

The preferred polymer is polyvinyl chloride. "Polyvinyl chloride" or "PVC," as used herein, includes homopolymers of vinyl chloride, as well as polymerization products of vinyl chloride and one or more co-monomers. Examples of PVCs include copolymers of vinyl chloride and ethylene and copolymers of vinyl chloride and propylene. The PVC resins can also be the polymerization product of vinyl chloride and an ester monomer having the formula $H_2C=C(R^1)C(=O)OR^2$, where $R^1$ and $R^2$ are, independently, $C_{1-12}$ alkyl. An example of such a resin is a copolymer of a vinyl chloride monomer and a methyl methacrylate monomer. These resins may be used alone or in combination. Examples of PVC resins include BCP 70 available from Borden Chemical, Shintech SE 1200 available from Shintech, OXY 240 available from Occidental Chemical, and Oxy 240 available from Oxychem.

The plasticizer is added to the polymeric composition to alter the physical properties of the PVC. Adding the plasticizer can improve, for example, the flexibility, brittle point, and processability of the PVC. Examples of plasticizers include trimelletates, polyesters, and halogenated aromatic esters, such as the brominated aromatic ester and the chlorinated aromatic ester listed above. A number of these plasticizers, however, are solids at room temperature, which makes blending them to the polymeric compositions difficult.

A preferred plasticizer includes a brominated aromatic ester and a chlorinated aromatic ester. Adding sufficient amounts of the chlorinated aromatic ester to the brominated aromatic ester can form a plasticizer that is liquid at room temperature and therefore good for blending with polymers. Preferably, the brominated aromatic ester is a tetrabromophthalate, and more preferably, the brominated aromatic ester is di-n-undecyl tetrabromophthalate. The chlorinated aromatic ester is preferably a tetrachlorophthalate, and more preferably, di-2-ethylhexyl tetrachlorophthalate. The plasticizer preferably includes about 20–80 weight percent tetrabromophthalate and about 20–80 weight percent tetrachlorophthalate; more preferably, about 35–65 weight percent tetrabromophthalate and about 35–65 weight percent tetrachlorophthalate; and even more preferably, about 45–55 weight percent tetrabromophthalate and about 45–55 weight percent tetrachlorophthalate. Tetrabromophthalate ester can be made as described above and is also available, for example, from Great Lakes Chemical Corporation. Tetrachlorophthalate can be made by direct esterification.

For 100 parts of PVC resin, the fire retardant PVC compositions preferably include from about 2 to about 35 parts of the preferred plasticizer, more preferably from about 5 to about 30 parts of plasticizer, and most preferably from about 10 to about 25 parts of plasticizer.

The clay filler can be a calcined aluminum silicate clay, a calcined kaolin clay or a combination thereof. Clay filler are available from, for example, JM Huber Corporation, Burgess Pigment Company, and Englehard Corporation. For 100 parts of the PVC resin, the compositions preferably include from about 2 to about 20 parts of clay filler, more preferably from about 4 to about 10 parts of clay filler, and most preferably about 5 parts of clay filler.

An example of a hydrated alumina is aluminum trihydrate. Hydrated aluminas are available from, for example, Alcoa Aluminum and Chemicals, Lonza and Pluess-Staufer Industries. For 100 parts of PVC resin, the compositions preferably include from about 10 to about 100 parts hydrated alumina and/or magnesium hydroxide, more preferably from about 20 to about 70 parts hydrated alumina and/or magnesium hydroxide, and most preferably about 40 parts hydrated alumina and/or magnesium hydroxide.

The compositions also can include a lead stabilizer that can react with chlorine produced from the PVC resin. For 100 parts of PVC resin, the compositions preferably include about 3 to about 12 parts of lead stabilizer, more preferably from about 5 to about 9 parts of lead stabilizer, and most preferably about 7 parts of lead stabilizer. Examples of lead stabilizers include dibasic lead phthalate, tetrabasic lead fumarate, tribasic lead sulphate and combinations thereof. Lead stabilizers are available from, for example, Hammond Corporation.

The compositions can include a carboxylic acid lubricant. For 100 parts PVC resin, the compositions preferably include from about 0.1 parts to about 0.5 parts carboxylic lubricant, more preferably from about 0.2 parts to about 0.4 carboxylic acid lubricant, and most preferably about 0.25 parts carboxylic acid lubricant. An example of a carboxylic acid lubricant is stearic acid, which is available from, for example, Henkel Corporation or Humko, a division of Witco.

The compositions can include a smoke suppressant containing zinc and molybdenum (i.e., a zinc/molybdenum smoke suppressant). For 100 parts of PVC resin, the compositions preferably include from about 5 to about 25 parts zinc/molybdenum smoke suppressant, more preferably from about 8 to about 15 parts zinc/molybdenum smoke suppressant, and most preferably about 10 parts zinc/molybdenum smoke suppressant. An example of a zinc/molybdenum smoke suppressant is Charmax LSZ4A available from R.J. Marshall Company.

The compositions can include a smoke suppressant containing zinc and antimony (i.e., a zinc/antimony smoke suppressant). For 100 parts of PVC resin, the compositions preferably include from about 2 part to about 15 parts zinc/antimony smoke suppressant, more preferably from about 3 to about 10 parts zinc/antimony smoke suppressant, and most preferably about 5 parts zinc/antimony smoke suppressant. Zinc/antimony smoke suppressants are available from Great Lakes Chemical Corporation and Amspec Corporation.

The compositions can include zinc borate. For 100 parts of PVC resin, the compositions preferably include from about 0.5 to about 10 parts zinc borate, more preferably from about 1 to about 4 parts zinc borate, and most preferably about 2 parts zinc borate. Zinc borate is available from, for example, Solutia, Anzon and U.S. Borax, Incorporated. The compositions are prepared according to conventional dry blend or wet blend methods known to those skilled in the art of PVC compounding. The mixtures obtained from the blending process can further be compounded with a mixer such as a BANBURY® batch mixer, extruder, or multiple screw extruder.

An exemplary composition of a fire retardant having a plasticizer including brominated aromatic ester and a chlorinated aromatic ester is compared below with a composition having di-2-ethyl-hexyl-tetrabromophthalate (Truflex 45) as a plasticizer. Samples were prepared and tested according to ASTM protocols.

| Formulation | | |
|---|---|---|
| PVC resin | 100 | 100 |
| Trimellitate plasticizer | 30 | 30 |
| Kaolin clay | 5 | 5 |
| Alumina trihydrate | 40 | 40 |
| Dibasic lead phthalate | 7 | 7 |
| Stearic acid | 0.25 | 0.25 |
| Antimony oxide | 5 | 5 |
| Di-2-ethyl-hexyl-tetrabromophthalate plasticizer (Truflex 45) | 15 | — |
| Tetrabromophthalate/tetrachlorophthalate plasticizer blend | — | 15 |
| Properties | | |
| Hardness (Inst/10 sec Del, Shore C) - ASTM D-2240 | 91/86 | 91/86 |
| Specific gravity - ASTM D-792 | 1.52 | 1.5 |
| Tensile strength (psi) - ASTM D-412 | 2990 | 2869 |
| Elongation at break (%) - ASTM D-412 | 200 | 191 |
| Brittleness temperature (° C.) - ASTM D-746 | −11.5 | −18.5 |
| Oxygen index (% $O_2$) - ASTM D-2863 | 40 | 39.5 |
| Arapahoe smoke (% decharred) - ASTM D-4100 | 5.57 | 5.00 |
| Arapahoe smoke (% not decharred) - ASTM D-4100 | 7.95 | 7.18 |

The data indicate that a plasticizer including a brominated aromatic ester and a chlorinated aromatic ester improves the brittleness temperature of a polymeric composition when used in place of Truflex 45. Preferably, the polymeric composition having a plasticizer including a brominated aromatic ester and a chlorinated aromatic ester has a brittleness temperature less than −12° C., an Arapahoe smoke (% decharred) value less than 5.50, and/or an Arapahoe smoke (% not decharred) value less than 7.75.

Other embodiments are within the claims.

What is claimed is:

1. A polymer composition, comprising:
   a polymer; and
   a plasticizer including a tetrabromophthalate and a tetrachlorophthalate.

2. The polymer composition according to claim 1, wherein the tetrabromophthalate is di-n-undecyl tetrabromophthalate.

3. The polymer composition according to claim 1, wherein the tetrachlorophthalate is di-2-ethylhexyl tetrachlorophthalate.

4. The polymer composition according to claim 1, wherein the brominated aromatic ester is a solid at room temperature and the chlorinated aromatic ester is a liquid at room temperature.

5. The polymer composition according to claim 1, wherein the plasticizer includes sufficient tetrachlorophthalate to make the plasticizer a liquid at room temperature.

6. The polymer composition according to claim 5, wherein the plasticizer includes about 20–80 weight percent of tetrabromophthalate and about 20–80 weight percent of tetrachlorophthalate.

7. The polymer composition according to claim 6, wherein the plasticizer includes about 35–65 weight percent of tetrabromophthalate and about 35–65 weight percent of tetrachlorophthalate.

8. The polymer composition according to claim 7, wherein the plasticizer includes about 45–55 weight percent of tetrabromophthalate and about 45–55 weight percent of tetrachlorophthalate.

9. The polymer composition according to claim 1, further comprising a clay filler.

10. The polymer composition according to claim 1, further comprising a hydrated alumina.

11. The polymer composition according to claim 1, further comprising a lead stabilizer.

12. The polymer composition according to claim 1, further comprising a carboxylic acid lubricant.

13. The polymer composition according to claim 1, further comprising a smoke suppressant.

14. The polymer composition according to claim 1, wherein the composition comprises:
  about 100 parts of polyvinyl chloride;
  about 2 to about 20 parts of a clay filler;
  about 10 to about 100 parts of a hydrated alumina;
  about 3 to about 12 parts of a lead stabilizer;
  about 0.1 to about 0.5 parts of a carboxylic acid lubricant;
  about 2 to about 15 parts of a smoke suppressant; and
  about 2 to about 35 parts of the plasticizer.

15. A cable jacket including the composition of claim 1.

16. A wire insulation including the composition of claim 1.

17. A method of making tetrabromophthalate, comprising:
  contacting a carboxylated, tetrabrominated aromatic compound with an alcohol, an esterification catalyst, sulfuric acid and a sulfuric acid deactivating compound capable of reacting with sulfuric acid to form a water insoluble sulfate compound,
  wherein the aromatic compound reacts with the alcohol to form the tetrabromophthalate while the deactivating compound reacts with sulfuric acid to form the water insoluble sulfate compound.

18. The method according to claim 17, wherein the carboxylated, tetrabrominated aromatic compound is selected from the group consisting of tetrabromophthalic anhydride, tetrabromophthalic acid and mixtures thereof.

19. The method according to claim 17, wherein the carboxylated, tetrabrominated aromatic compound comprises tetrabromophthalic anhydride.

20. The method of claim 18, further comprising contacting an esterification catalyst deactivating compound.

21. The method of claim 17, further comprising contacting an anti-oxidant.

22. The method of claim 17, wherein the sulfuric acid deactivating compound comprises barium acetate.

23. The method of claim 17, wherein the alcohol comprises 2-ethylhexyl alcohol.

24. The method of claim 17, wherein the alcohol is selected from the group consisting of linear alcohols, non-linear alcohols and mixtures thereof.

25. A method of making tetrabromophthalate, comprising:
  contacting tetrabromophthalic anhydride, an alcohol, barium acetate, sulfuric acid and an esterifying catalyst,
  wherein the tetrabromophthalic anhydride reacts with the alcohol to form tetrabromophthalate while the barium acetate reacts with the sulfuric acid to form barium sulfate.

26. The method of claim 25, further comprising contacting an anti-oxidant.

27. The method of claim 26, wherein the alcohol is 2-ethylhexyl alcohol.

28. The method of claim 27, further comprising deactivating the esterification catalyst.

29. The method of claim 25, further comprising contacting an esterification catalyst deactivating compound.

30. The method of claim 25, wherein the alcohol comprises 2-ethylhexyl alcohol.

31. The method of claim 25, wherein the alcohol is selected from the group consisting of linear alcohols, non-linear alcohols and mixtures thereof.

32. A method of esterifying a carboxylated, halogenated aromatic compound, comprising:
  contacting the carboxylated halogenated aromatic compound with an alcohol, an esterification catalyst, sulfuric acid and a sulfuric acid deactivating compound capable of reacting with sulfuric acid to form a water insoluble sulfate compound,
  wherein the aromatic compound reacts with the alcohol to form the tetrabromophthalate while the deactivating compound reacts with sulfuric acid to form the water insoluble sulfate compound.

33. The method of claim 32, further comprising contacting an esterification catalyst deactivating compound.

34. The method of claim 32, further comprising contacting an anti-oxidant.

35. The method of claim 32, wherein the sulfuric acid deactivating compound is barium acetate.

36. The method of claim 17, further comprising contacting water with the esterification catalyst.

37. The method of claim 25, further comprising contacting water with the esterification catalyst.

38. The method of claim 32, further comprising contacting water with the esterification catalyst.

39. The polymer composition according to claim 1, wherein the polymer is polyvinyl chloride.

* * * * *

Disclaimer 6,232,427—John A. Buono, Riverside; Maryellen Cobb, Warwick, both of RI (US); Tao T. Tao, North Attleboro, MA (US). Esterification Method. Patent dated May 15, 2001. Disclaimer Filed August 9, 2001, by the assignee, Teknor Apex Company.

Hereby enters this disclaimer to claims 1-16 and claim 39 of said patent.

*(Official Gazette, November 6, 2001)*

(12) INTER PARTES REEXAMINATION CERTIFICATE (2nd)
United States Patent
Buono et al.

(10) Number: US 6,232,427 C1
(45) Certificate Issued: Mar. 2, 2004

(54) ESTERIFICATION METHOD

(75) Inventors: John A. Buono, Riverside, RI (US); Maryellen Cobb, Warwick, RI (US); Tao T. Tao, North Attleboro, MA (US)

(73) Assignee: Teknor Apex Company, Pawtucket, RI (US)

Reexamination Request:
No. 95/000,001, Jul. 27, 2001

Reexamination Certificate for:
Patent No.: 6,232,427
Issued: May 15, 2001
Appl. No.: 09/470,613
Filed: Dec. 22, 1999

Disclaimer of Claims 1 through 16 and 39 Filed Aug. 9, 2001 (Paper No. 5, O.G. citation Nov. 6, 2001).

Related U.S. Application Data

(63) Continuation-in-part of application No. 09/199,691, filed on Nov. 25, 1998, now abandoned.
(60) Provisional application No. 60/067,970, filed on Dec. 8, 1997.

(51) Int. Cl.[7] .......................... C08L 27/06; C08G 14/02; C08K 5/12; C07C 69/80; C07C 67/08
(52) U.S. Cl. ........................ 528/147; 524/284; 524/288; 560/83
(58) Field of Search ................................. 524/284, 288; 560/83; 528/147

(56) References Cited

U.S. PATENT DOCUMENTS

| | | | | |
|---|---|---|---|---|
| 3,878,237 A | * | 4/1975 | Eggensperger et al. ...... | 558/378 |
| 4,892,683 A | | 1/1990 | Naseem ....................... | 252/609 |
| 5,036,121 A | | 7/1991 | Coaker et al. ............... | 524/100 |
| 5,120,781 A | * | 6/1992 | Johnson, Jr. ................. | 524/274 |
| 5,393,820 A | * | 2/1995 | Ashworth et al. ........... | 524/466 |
| 5,760,161 A | | 6/1998 | Goins, Jr. et al. ........... | 528/299 |
| 5,824,241 A | * | 10/1998 | Horvat ........................ | 252/609 |
| 6,114,425 A | | 9/2000 | Day et al. ................... | 524/288 |
| 6,337,419 B1 | | 1/2002 | Day et al. ..................... | 560/83 |

FOREIGN PATENT DOCUMENTS

JP 75-5701 5/1975

OTHER PUBLICATIONS

Lange's Handbook of Chemistry, 12th ed., pp. 5–7 and 5–8 (1979).
Great Lakes Chemical Corporation, Certificate of Analysis, Tetrabromophthalic anhydride PHT–4, Lot No. 632323I–1 (Oct. 10, 1994).
Great Lakes Chemical Corporation, Certificate of Analysis, Tetrabromophthalic anhydride PHT–4, Lot No. 634103I–1 (Oct. 13, 1994).
"TYZOR Titanates", Du Pont Performance Products (Apr. 1987).
"TILCOM® Catalysts for Ester Manufacture", Tioxide UK Limited (Oct. 1984).
Barfurth, "Manufacture of Ester Plasticizer by Means of Alkyl Titanates as Esterification Catalyst", Application Research Department ZP–NPA (1992).

\* cited by examiner

Primary Examiner—Rabon Sergent

(57) ABSTRACT

Methods of making halogenated aromatic esters are described. Polymer compositions including halogenated aromatic esters are also described. In one embodiment, the method includes contacting a tetrabromophthalate, an alcohol and barium acetate.

INTER PARTES REEXAMINATION CERTIFICATE ISSUED UNDER 35 U.S.C. 316

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1–16 and 39 are now disclaimed.

Claims 17–38 are cancelled.

\* \* \* \* \*